(12) United States Patent
Goldberg et al.

(10) Patent No.: US 10,542,936 B2
(45) Date of Patent: Jan. 28, 2020

(54) CARRIER SYSTEM FOR AN OBJECT WORN ON THE BODY AND METHOD OF PRODUCTION

(71) Applicant: Roche Diabetes Care, Inc., Indianapolis, IN (US)

(72) Inventors: Norman Goldberg, Düsseldorf (DE); Michael Herbertz, Wermelskirchen (DE); Oliver Kube, Worms (DE); Ralf Nittenwilm, Höhr-Grenzhausen (DE); Helmut Walter, Heppenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 136 days.

(21) Appl. No.: 15/093,503

(22) Filed: Apr. 7, 2016

(65) Prior Publication Data
US 2016/0213322 A1   Jul. 28, 2016

Related U.S. Application Data

(63) Continuation of application No. PCT/EP2014/071671, filed on Oct. 9, 2014.

(30) Foreign Application Priority Data

Oct. 10, 2013   (EP) ..................................... 13188144

(51) Int. Cl.
*A61B 5/00*   (2006.01)
*A61M 25/02*   (2006.01)
(Continued)

(52) U.S. Cl.
CPC .......... *A61B 5/6833* (2013.01); *A61L 24/046* (2013.01); *A61L 24/06* (2013.01);
(Continued)

(58) Field of Classification Search
CPC .............. A61M 25/02; A61M 5/14248; A61M 2025/0266; A61M 2005/3022; A61B 5/6833
See application file for complete search history.

(56) References Cited

U.S. PATENT DOCUMENTS 3,953,566 A * 4/1976 Gore ...................... B01D 71/36
264/505
4,359,051 A * 11/1982 Oczkowski ............. A61F 5/448
604/339
(Continued)

FOREIGN PATENT DOCUMENTS

EP   2 636 417 A1   9/2013

OTHER PUBLICATIONS

English translation of International Preliminary Report on Patentability, PCT/EP2014/071671, dated Jan. 21, 2016.

*Primary Examiner* — Emily L Schmidt
(74) *Attorney, Agent, or Firm* — Bose McKinney & Evans LLP

(57) ABSTRACT

The invention relates to a carrier system for an object worn on the body, comprising a flexible carrier plaster, which has a flat carrier layer and an adhesive layer, applied to the lower face of said carrier layer, which adhesive layer adheres to the skin of a body part when pressed thereon, the adhesive layer consisting of a pressure-sensitive adhesive, and further comprising, on the upper face of the carrier layer facing away from the skin, a rigid mounting platform. According to this disclosure, a joining region of the mounting platform is permanently joined to the upper face of the carrier layer via a structural adhesive connection that consists of a structural adhesive.

19 Claims, 2 Drawing Sheets

(51) Int. Cl.
*A61L 24/04* (2006.01)
*A61L 24/06* (2006.01)
*B29C 65/48* (2006.01)
*A61M 5/142* (2006.01)
*B29L 31/00* (2006.01)

(52) U.S. Cl.
CPC ......... *A61M 25/02* (2013.01); *B29C 65/4825* (2013.01); *B29C 65/4845* (2013.01); *A61B 2562/12* (2013.01); *A61M 5/14248* (2013.01); *A61M 2025/0266* (2013.01); *B29L 2031/753* (2013.01)

(56) References Cited

U.S. PATENT DOCUMENTS

| | | | | |
|---|---|---|---|---|
| 5,267,967 | A * | 12/1993 | Schneider | A61M 25/02 128/DIG. 6 |
| 6,452,063 | B1 * | 9/2002 | Curro | A61F 13/49011 428/131 |
| 7,727,615 | B2 * | 6/2010 | Kato | C09J 7/22 428/137 |
| 2003/0125668 | A1 * | 7/2003 | Bierman | A61M 25/02 604/174 |
| 2005/0220852 | A1 * | 10/2005 | Shirai | A61K 9/7053 424/449 |
| 2007/0282271 | A1 * | 12/2007 | Kaplan | A61F 5/445 604/174 |
| 2008/0249476 | A1 * | 10/2008 | Bierman | A61M 25/02 604/175 |
| 2009/0076453 | A1 | 3/2009 | Mejlhede et al. | |
| 2009/0093779 | A1 * | 4/2009 | Riesinger | A61F 13/00029 604/290 |
| 2009/0182283 | A1 * | 7/2009 | Sloan | A61M 25/02 604/180 |
| 2009/0216103 | A1 * | 8/2009 | Brister | A61B 5/14532 600/347 |
| 2011/0166529 | A1 * | 7/2011 | LeLievre | A61M 25/02 604/180 |
| 2011/0275997 | A1 | 11/2011 | Booma et al. | |
| 2015/0038892 | A1 * | 2/2015 | Marmaras | A61F 13/00021 602/43 |
| 2015/0045752 | A1 | 2/2015 | Grillitsch et al. | |

* cited by examiner

CARRIER SYSTEM FOR AN OBJECT WORN ON THE BODY AND METHOD OF PRODUCTION

RELATED APPLICATIONS

This application is a continuation of PCT/EP2014/071671, filed Oct. 9, 2014, which claims priority to EP 13188144.3, filed Oct. 10, 2013, both of which are hereby incorporated herein by reference in their entireties.

BACKGROUND

The invention relates to a carrier system for a body-worn object, in particular a medical instrument with a flexible carrier plaster comprising a sheetlike carrier ply and on the lower side thereof an adhesive layer comprising a pressure sensitive adhesive and adherent to the skin of a body part by contact pressure, and with a specifically rigid assembly platform arranged on the skin remote upper side of the carrier ply. The invention further relates to a method of producing and to the special method of using such a carrier system.

Such medical devices and applications generally require the highest possible degree of quality and reliability. The materials used for this have to meet a wide diversity of needs: they need to be, for example, biologically compatible and/or inert as well as corrosion and temperature resistant and they need to work flawlessly under a very wide range of conditions. This dictates strict requirements to be met by such systems and their method of making. Adhesives like all other materials directly employed on the human body in the field of medicine have to conform not just to very high quality standards but also to various statutory regulations; the same applies to the manufacturing operation as a whole.

A known biomedical engineering solution in the field of continuous glucose monitoring (CGM), insulin delivery systems (IDS) and electroencephalography (EEG) probes is to connect the carrier plaster and the instrument by ultrasonic welding. "Standard plasters" comprising fleece are employed here, reaching a wear period of up to 4 days and in some cases even 5 days. Such standard plasters have a maximum pressure sensitive adhesive add-on of less than 80 g/m$^2$. Owing to the long period of wear or the high load on the body, the plasters gradually become detached starting at the edge. Patients trying to achieve a long period of wear in particular constantly have to restick or overstick the plasters, or else the plasters fail prematurely. The cause for this early failure resides not only in the use of standard plasters, which are not designed for such a long period of wear, but also in the bonding technique of ultrasonic welding. This involves the punctuate input of high heat causing the carrier material, which consists of plastic, to melt slightly (T greater than 130° C.). But this leads to some local decomposition of the carrier material, thereby reducing the effective adherend surface and causing internal stresses to build up in the adhesive film. Since visco-elastic systems are concerned, this leads to detachment of the plaster from the body. The effective adherend surface of the plaster with regard to the body is diminished as a result. This is frequently the case in the region underneath the medical instrument, which is actually supposed to adhere particularly well to the skin given the envisioned function, for example contact adherence of a skin electrode.

EP-A 1 923 081 discloses an infusion device for insulin, said device comprising a catheter head which is attachable to the skin via a plaster and on its upper side has a connector to releasably and rotatably plug in an insulin pump, wherein complete attachment to the body is only established by direct tacky attachment to the skin of peripheral regions of the insulin pump which extend beyond the plaster. Unspecified skin-compatible adhesives are said to be employed. While wear-appropriate orientation of the pump on the body is achievable as a result, secure attachment does require the employment and handling of additional skin adhesives at the use site.

US 2011/257997 A1 describes a device for medicating a patient, the device comprising a two-part housing comprising a base part for attachment to the skin and an upper part which is mobile and connectable thereto, the two parts being releasably connected via a positive mechanical form-fit or optionally adhered together. As a joining region, only protruding molded structures are disclosed, rendering manufacture and assembly rather costly and inconvenient.

SUMMARY

Proceeding from the above, this disclosure addresses the problem of further improving the prior art systems and processes and of devising a high level of non-slip performance for a very long and reliable level of wear performance coupled with simplified ease of manufacture and uncomplicated attachment.

The concept of this disclosure is to connect the to-be-worn object in a manner that impairs the pressure sensitive adhesive layer of the plaster as little as possible. Accordingly, this disclosure provides that a joining or structuring region of the assembly platform firmly connects to the upper side of the carrier ply via a structural (constructional) type of adhesive bond comprising a structural adhesive. Such a firm bond due to a structural type of adhesion can only be broken destructively, whereas pressure sensitive adhesion is in principle reversible.

Structural adhesives is generally the designation for adhesives that are employed in a joining connection which thereby acquires significant importance in ensuring the stability and/or functioning of the component part. Constructional types of adhesive bonds and/or structural types of adhesive are also referred to in this context. The rule of thumb is that a structural type of adhesive bond has a shear strength of more than 2 N/mm$^2$. By contrast, a pressure sensitive adhesive is a species of adhesive which, in the solvent-free state and particularly at room temperature, offers a visco-elastic type of adhesion and on direct contact adheres to a multiplicity of surfaces in that pressing down on the surface of the adherend parts brings about a form of wetting which results in adequate forces of adherence.

The structural type of adhesive bond between the assembly platform/baseplate and the plaster ensures that the pressure sensitive adhesive layer on the plaster (establishing the bond to the body) is not destroyed. As a result, the worn object is held in place by the full force of adhesiveness being available from the large effective adherend area. Lower levels of shear stress between body and plaster are obtained owing to the maintained flexibility of the carrier material. Edge detachment of the plaster is also reduced and a longer period of wear without loss of the system is achieved. User restrictions in common everyday situations are minimized, and the improved wearing comfort ensures better acceptance.

The carrier plaster advantageously is protected by a release liner, preferably one removable by means of a projecting tab, which covers the adhesive layer on its sticky side before application. The release liner in question may also be constructed in two or more parts.

In a further advantageous embodiment, the upper side face of the carrier ply attaches flatly to a facing lower joining area of the assembly platform via structural adhesive, so a simple form of assembly and a reliable undissoluble attachment of the platform without impairment of the pressure sensitive adhesive layer is achieved.

Preferably, the carrier ply consists of foil material or textile material or a foam or a combination thereof, so a sheetlike conformation to a skin contour which is not uniform is possible.

In order to obtain high flexibility coupled with good water vapor permeability, it is favorable for the carrier ply to consist of a thermoplastic (single or multilayered), preferably microperforated foil.

To be sufficiently stretchable, the carrier ply should have a maximum elastic modulus of less than 10 N/mm$^2$, preferably less than 5 N/mm$^2$.

Advantageously, the adhesive layer has a pressure sensitive adhesive application of 80 to 120 g/m$^2$, preferably of 100 to 110 g/m$^2$. The background is that human skin has a high level of surface roughness (due to, for instance, dead particles of skin, furrows, etc.) and the adhesive can penetrate (flow) into deeper layers of the skin. Raising the adhesive quantity to more than 80 g/m$^2$ is accordingly helpful to improve the level and length of adherence to human skin.

In a further advantageous embodiment, the adhesive layer is formed by a pressure sensitive adhesive based on acrylate, silicone, rubber, thermoplastic elastomer, hydrogel, polyurethane, polysiloxane, vinyl acetate or mixtures thereof. It is preferred to use an acrylate-vinyl acetate copolymer as pressure sensitive adhesive.

In view of the demands for a longer period of wear coupled with enduringly good adherence to the skin as well as pain- and residueless detachment, breathability and hence the water vapor permeability (MVTR, "Moisture Vapor Transmission Rate") plays a decisive part. This water vapor permeability may be determined in accordance with DIN EN 13726-2 at a temperature of 37° C. and an atmospheric humidity of 18%. Advantageously, the carrier ply and/or the adhesive layer of the carrier plaster has an MVTR value of more than 400 g/m$^2$ in 24 h.

To obtain a high level of strength, it is advantageous if the structural type of adhesive bond comprises a structural adhesive based on cyanoacrylate adhesive, epoxy adhesive or polyurethane adhesive.

Owing to the long duration of wear on the body, the pressure sensitive adhesive and the structural adhesive should have a biocompatible composition approved for medical applications.

Advantageously, the assembly platform is formed by a plastic molding preferably of polycarbonate.

This disclosure also provides a medical instrument comprising a carrier system as described above.

In process terms, this disclosure teaches a method of producing a carrier system for a body-worn object, comprising the steps of:
  providing a carrier plaster preferably as a die-cut part consisting of a carrier ply, an adhesive layer and a release liner,
  applying a structural adhesive as an adhesive bead to an joining region of an assembly platform,
  contacting the joining region with the skin-remote upper side of the carrier plaster to form a structural type of adhesive bond.

In order to obtain a constructional type of material bond, it is advantageous for the assembly platform to be pressed against the plaster during the cure of the structural adhesive.

An additional improvement is achievable when the structural adhesive is dried/cured in a forced manner optionally by irradiation after contacting, to acquire its full joining strength.

A further aspect of this disclosure relates to the method of using a carrier system of this disclosure for at least one application from the following group:
  sensorially monitoring and/or capturing a body parameter,
  administering active ingredients, in particular insulin to or through the skin,
  providing a body entry port or body exit port,
  wearing body jewelry.

BRIEF DESCRIPTION DRAWINGS

The above-mentioned aspects of exemplary embodiments will become more apparent and will be better understood by reference to the following description of the embodiments taken in conjunction with the accompanying drawings, wherein.

DESCRIPTION

Figure 1:
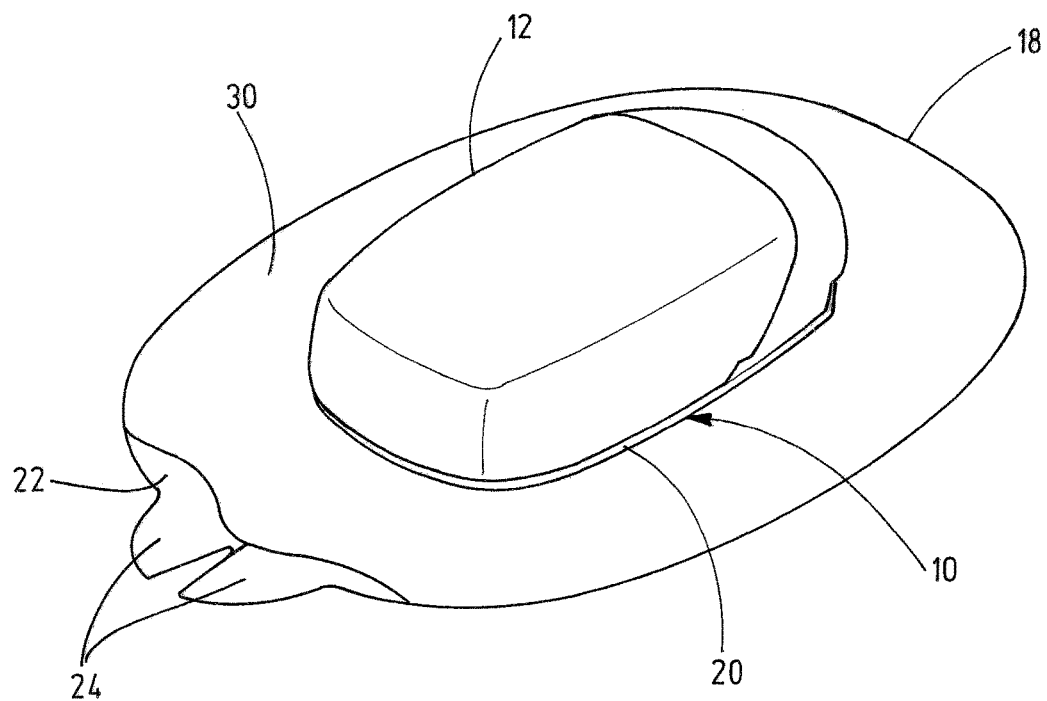
FIG. 1 shows a carrier system with a medical instrument for pressure sensitive adhesive attachment to the skin in a perspective view.

The embodiments described below are not intended to be exhaustive or to limit the invention to the precise forms disclosed in the following description. Rather, the embodiments are chosen and described so that others skilled in the art may appreciate and understand the principles and practices of this disclosure.

The carrier system 10 depicted in the drawing is designed for pressure sensitive adhesive attachment of a medical instrument 12 for diagnostic long term applications to the skin 14 of a body part 16 and for this purpose comprises a carrier plaster 18 and a rigid assembly platform 20 arranged on its skin remote upper side. The self adhesive lower side of the carrier plaster 18 is before use covered by a two part release liner 22 which is simple to remove by means of projecting tabs 24.

Figure 2:
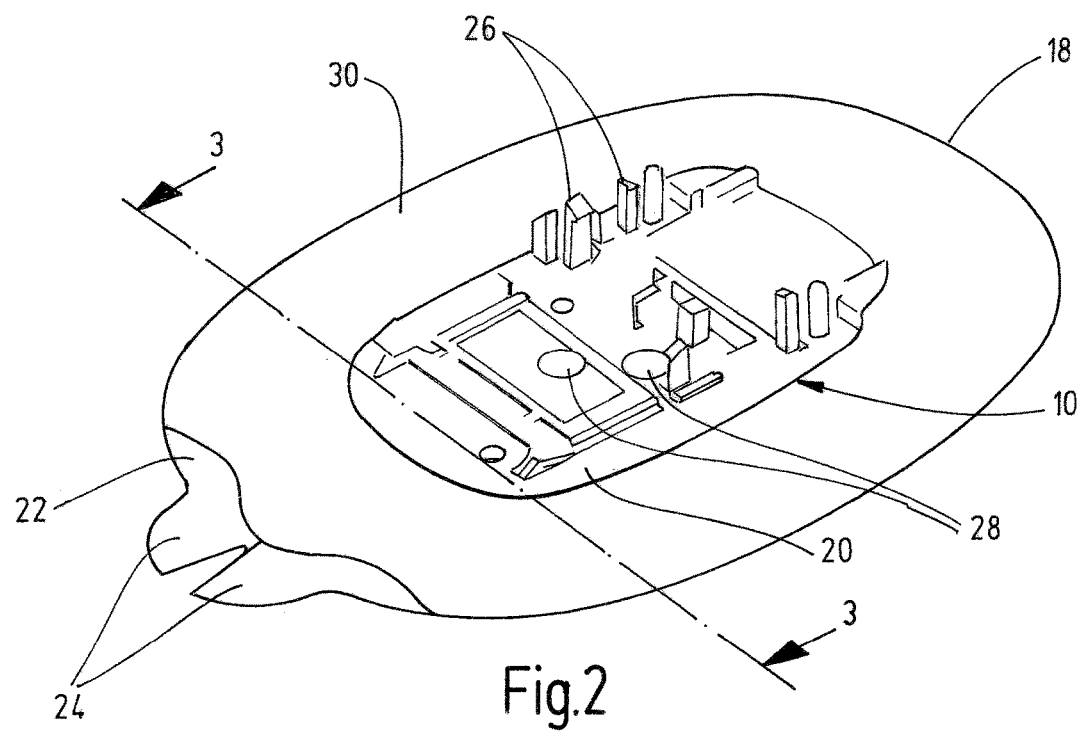
FIG. 2 shows the carrier system with an assembly platform in a depiction corresponding to FIG. 1.

As is apparent from FIGS. 1 and 2, the assembly platform 20 makes it possible to mount instrument 12 via form fit means 26. The permanently attached assembly platform 20 may also be an integral constituent part of instrument 12. Such an instrument and/or appliance may be a diagnostic measuring system for example for continuous glucose monitoring, a sensor or a delivery device for pharmaceuticals for example in the form of an insulin pump, or else contain an electronic subassembly such as an RFID chip. Further conceivable applications consist of organ monitoring, for example the glomerular filtration rate for checking the renal function, or the performance of lactate tests.

In the illustrated embodiment, the assembly platform is formed by a plate type plastic molding for example of polycarbonate. Apertures 28 in the assembly platform 20 and the plaster region underneath provide direct access to and/or exit from the skin.

Figure 3:
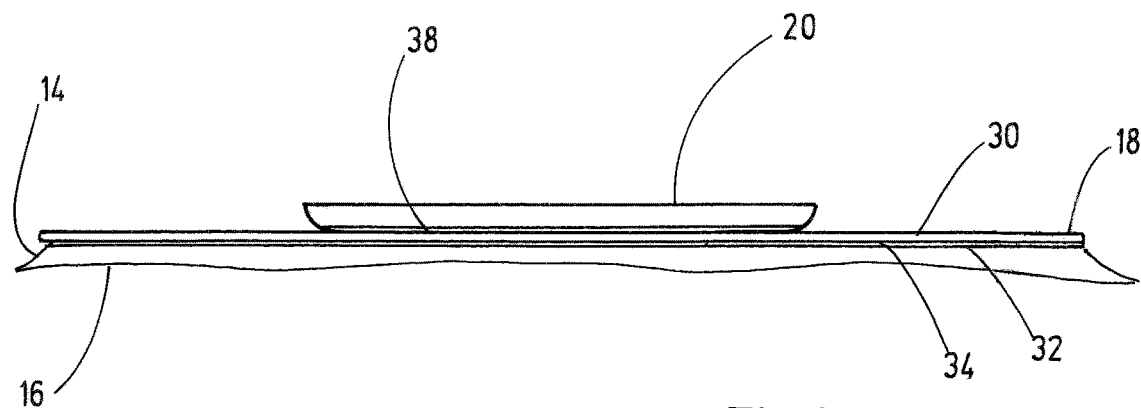
FIG. 3 shows a section through the carrier system along the line 3-3 of FIG. 2 in the adhered state on the skin.
Figure 4:
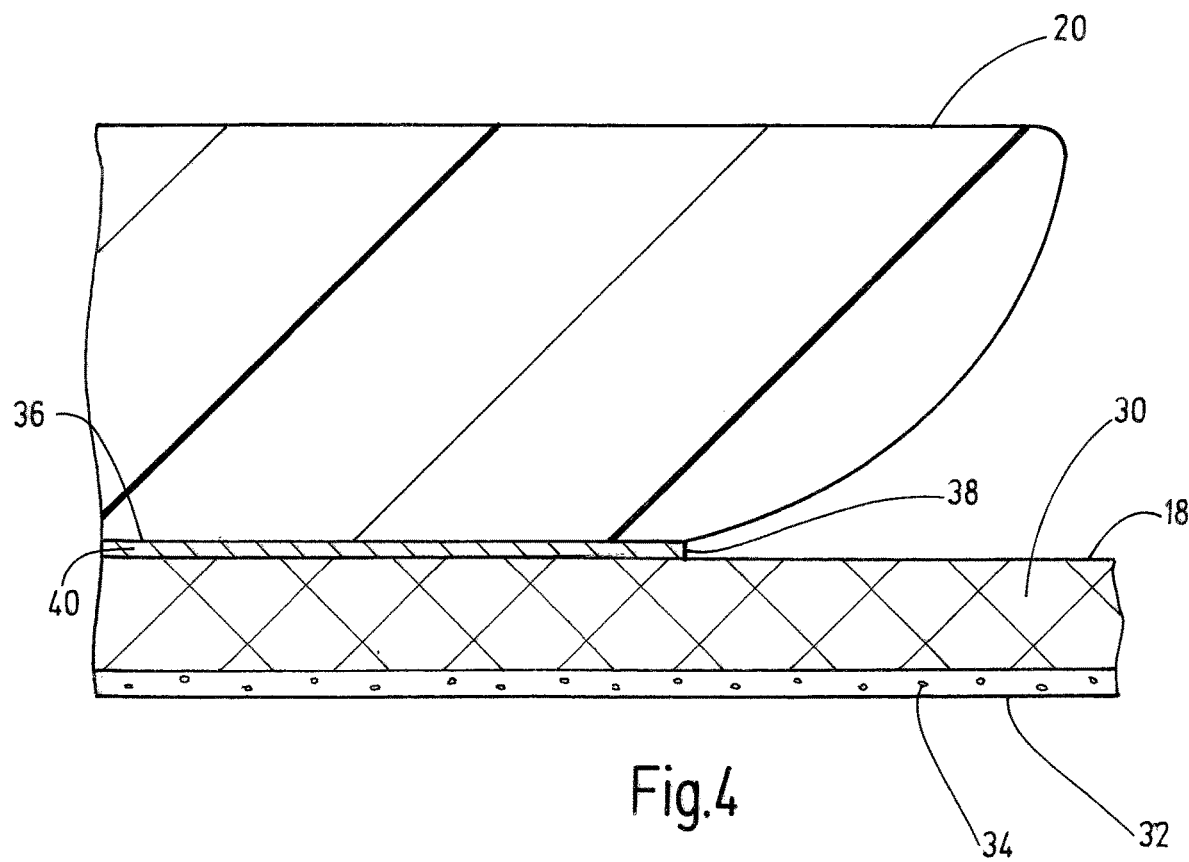
FIG. 4 shows an enlarged detail from FIG. 3.

As best seen in FIGS. 3 and 4, the carrier plaster 18 comprises a sheetlike flexible carrier ply 30 and on the lower side thereof an adhesive layer 32 comprising a pressure sensitive adhesive 34 and adherent to the skin 14 by contact pressure. The rigid assembly platform 20 is permanently secured on the skin remote upper side of the carrier ply 30 in a structuring region 36, configured as lower joining area, via a constructional or structural type of adhesive bond 38 comprising a structural adhesive 40.

An essential requirement expected of a carrier plaster 18 attachable to skin is that the adhesive used therefore should be skin compatible and/or biocompatible, for example in accordance with DIN ISO 10993. This includes particularly also a very low residual monomer content so as to rule out any cytotoxic or skin irritating effect. With a view to long term applications, for example applications for a period of up to seven days, further requirements become important, including the in principle initially contradictory demands for a rapid, durable, firm adhesive attachment which does not detach or slip even in everyday situations, for example during exercise, showering, bathing or else in a sauna, or hinder the wearer in any way—and which furthermore should also be pressureless and not interfere with the skin's microcirculation, and the demand for clean, residueless detachability of the plaster following prolonged use.

Acrylate-based pressure sensitive adhesives are one class of adhesives which are usable in this context. The advantage of these materials resides in their outstanding adherence, the good tolerance of the ingredients by human skin, the low sensitization tendency and the very good resistance to sterilizing temperatures and aging.

Alternatively, high molecular weight acrylate pressure sensitive adhesives may be combined with plasticizing additives for use as adhesives. The use of plasticizing ingredients cooperates with the high molecular weight polymer matrix to ensure secure adherence to human skin. However, the migration tendency of plasticizing components has to be taken into account here. It can result in nonuniform peeling behavior off the skin as a consequence of mixing two components having differing adherent behavior.

Silicone gel adhesives can also be employed for adhesive bonds to skin. They have the advantage that they can be easily peeled off the skin even after a long period of wear and without damaging the skin. With acrylate based pressure sensitive adhesives, however, adhesive force and water vapor permeability are down. Moreover, the production of interrupted layers of adhesive is technologically trickier with these pressure sensitive adhesives.

A further adhesive alternative for adhesive bonds in the medical, dermatological or cosmetic sector is represented by thermoplastic elastomers based on a block copolymer having a styrene-olefin-styrene block, a tackifier and also generally a plasticizer and an amphiphilic copolymer. It must be borne in mind here that plasticizer migration may impair not only the adhesive force but also the appearance of a plaster, and that such adhesives may in certain circumstances have an occlusive effect whereby the skin is hermetically sealed off.

Adhesives in principle employable for the present purposes are adhesives based on synthetic rubber, in particular on polyisobutylene and then preferably in admixture with a styrene-isoprene-styrene block copolymer and/or in the form of a styrene-isobutylene-styrene block copolymer. Adhesives of this type may have additives such as resins in particular added to them to improve their sticking properties.

Hydrogels are a further class of adhesives for medical applications. They contain a high proportion of water and natural polymers having high molecular weights, for example polysaccharides such as glucomannan, galactomannan, carrageenan or alginate, or else synthetic polymers often crosslinked for cohesive purposes, for example copolymers based on 2-acrylamido-2-methylpropanesulfonic acid.

Adhesives based on polyurethane or polysiloxane are other adhesives useful in principle for the purposes of this disclosure.

The type of adhesive which has been found to be best with regard to the stated requirements and in particular also with regard to a very low residual monomer content is a pressure sensitive adhesive comprising one or more polymers prepared from olefinic monomers and having a residual free monomer content of less than 0.01 wt %. The polymers in question may be present as homopolymer, copolymer or block polymer or as a mixture of various homo-, co- and/or block polymers. They may contain further substances such as, in particular, tackifying resins, preferably hydrogenated rosin. A copolymer formed from 2-ethylhexyl acrylate and vinyl acetate has turned out to be particularly advantageous for the desired properties of a pressure sensitive adhesive. Since esters of acrylic acid are α,β-unsaturated carbonyl compounds, they are subject to Michael addition. For a prolonged wear period of seven days or more, the adhesive should only have a minimal residual monomer concentration in order not to be cytotoxic and/or skin irritating, which is the case with the abovementioned residual monomer content.

In view of the demands for a longer period of wear coupled with enduringly good adherence to the skin as well as pain- and residueless detachment, breathability and hence the water vapor permeability (MVTR, "Moisture Vapor Transmission Rate") of sticky systems also plays a decisive part. This water vapor permeability may be determined in accordance with DIN EN 13726-2 at a temperature of 37° C. and an atmospheric humidity of 18% or in accordance with ASTM E 96 by the upright cup method at a temperature of 23° C. and an atmospheric humidity of 50%.

Water vapor permeability is accordingly to be understood as meaning rate per unit time at which moisture can pass through a membrane in the form of water vapor. The higher the MVTR value is, the greater the effectiveness is with which moisture under a wound dressing can be prevented. Since skin transpires and accordingly is a source of moisture, a lack of breathability can lead to overhydration and, as a consequence thereof, to some softening of the skin or else promote an unwanted process of plaster detachment. In conventional plaster systems, consisting before use of a liner covered adhesive layer and also a carrier material, it has hitherto been predominantly the adhesive components, the thickness of the adhesive layer or else its structure resulting for example from a discontinuous application of adhesive which have been considered as primarily decisive for the water vapor permeability of the overall system—the carrier itself played a minor part. Since, however, the carrier plasters of this disclosure are covered on both sides, the constitution of the carrier ply 30 acquires a distinctly larger significance also with regard to the MVTR values of the overall system.

In order to durably adhere to the skin for several days, in particular at least seven days in a manner which is reliable under all possible conditions and nonetheless at the same time have an MVTR rate which allows the skin to breathe and on ingress of moisture does not cause the plaster to detach, the pressure sensitive adhesive add-on should be at least 80 g/m². The upper limit is about 120 g/m², which has economic and technical reasons. A pressure sensitive adhesive add-on of 110 g/m² is preferred. At the adhesive layer thickness resulting therefrom, the MVTR rate thereof is above about 400 g/m² in 24 h.

The requirements expected of a pressure sensitive adhesive for attachment to skin apply in principle also to the material to be used for the carrier ply 30. Even when carrier materials employed in this context do not have any direct skin contact, it is nonetheless possible for constituent parts of carrier materials to migrate into and/or even through the adhesive layer and thereby come into contact with the skin. For this reason, the carrier materials should also only contain ingredients that are skin tolerated and minimally sensitizing, if at all. Further requirements consist in the inherently contradictory expectations of a certain flexibility/elasticity on the one hand and a certain stiffness on the other. Flexibility and elasticity is necessary for any conformation to a nonuniform skin contour and for secure material attachment even to the moving skin in order not to resist the movement of the skin and avoid the sensation of a foreign body. Stiffness is necessary for the die cutting operation in the manufacturing process and also for ensuring secure and rapid attachment of the object to be worn.

Carrier materials meeting the stated requirements in principle may consist for example of a multiplicity of polymeric compositions capable of forming low friction, flexible polymeric foils, for example from polyolefins such as polyethylene, polypropylene or polybutylene, from vinyl copolymers such as polyvinyl chloride or polyvinyl acetate, from olefin copolymers or else from acrylic polymers and copolymers. Mixtures or blends formed from plastically deformable or from plastically deformable and elastomeric materials such as, for example, polypropylene and polyethylene, polyurethane and selectively polyolefin, polycarbonate or polyester may likewise be used, as may purely TPE or TPU foils. The carrier ply 30 may take the form of a single- or multilayered foil. It can be produced using conventional methods of foil manufacture, e.g., by extrusion, coextrusion, casting from solvent, foaming.

Textile materials such as knits or wovens and also foams are likewise in principle useful as material for the carrier ply 30, as are combinations of the materials referred to.

Having regard to the inherently contradictory criteria of flexibility and stiffness, the thickness of the carrier ply 30 may be in the range from 2 μm to 250 μm. The carrier ply preferably has a thickness of less than 30 μm. The water vapor permeability of the carrier material should be at least 400 g/m² in 24 h.

A foil for use as carrier ply may be monolithic provided it exhibits the requisite water vapor permeability. However, the carrier ply may also be microporous or otherwise holey in order to render an otherwise water vapor impermeable polymeric foil water vapor permeable. Foils formed from the materials referred to have in principle only a very low MVTR value. To remedy this, such foils may be perforated to thereby acquire a sufficient degree of water vapor permeability. But a uniform and evenly microperforated thermoplastic foil limits the MVTR of the skin side pressure sensitive adhesive to the areas of the foil which are open due to the perforation; therefore, the purpose of a suitable perforation should be to provide as large a water vapor permeable area as possible. On the other hand, the perforation should not adversely affect the foil stiffness needed to immobilize the instrument and at the same time the perforation openings on the skin remote side of the carrier foil should only be minimally impaired if at all by the adhesive add-on for the structural type of adhesive bond.

Having regard to the high MVTR rate desired, it is particularly a microperforated thermoplastic foil with selectively different perforation geometries which is contemplated for use as carrier material. Perforation geometries particularly suitable for the present purpose are uniformly or nonuniformly (with some bulging for example) conically shaped geometries where the opening with the larger diameter should be on the skin facing side in order thereby to ensure a very large surface area for the permeability of water vapor from the skin side adhesive layer and ideally prevent at the same time the penetration of adhesive into the openings on the skin remote side. This larger opening may have a triangular, round or arbitrarily polygonal shape. The perforations preferably have the shape of a truncated cone. It is also possible for two or more different perforation geometries to be combined with each other in one foil.

To improve attachment of the adhesive to the plastics foil, the application of adhesive thereto may be preceded by subjecting said foil to an appropriate pretreatment in the form of, for example, a corona or plasma pretreatment or the application of a suitable primer, or an etching treatment.

A further alternative to obtain good attachment of the adhesive to the carrier material and a high MVTR value consists in employing a multi-ply carrier material, for example by lamination of suitable materials with a microperforated foil or by coextrusion and subsequent microperforation of different materials in one foil. When a plastics foil is laminated together with another material, their water vapor permeability commends fibrous nonwoven web fabrics or other textiles. A conventional method of lamination may be used, for example one involving heating or one involving the use of an adhesive. Useful carrier materials likewise include plastics coated fiber materials where at least the plastics coating is appropriately perforated. The textile side of the textile incorporating carrier material may in accordance with its suitability be positioned not only on the skin facing side of the carrier material but also on the skin remote side.

In addition to the discussed plastics foils or combinations comprising plastics foils, purely textile carriers are also usable as carrier ply 30. These textiles may be employed in the form of fibrous nonwoven web fabrics or in woven form, stitched form or loop-drawingly knitted form; in principle, the form in which the fibers are bound or bonded to each other is freely choosable. The starting material for these textile carriers may consist of natural or synthetic polymers, for example cellulose, silk or cotton as natural polymers or polyvinyl chloride, polyurethane, polyester, polyamide, Nomex, Kevlar, polypropylene, acrylic, Preox, nylon or rayon as synthetic polymers.

A transversely elastic woven or loop-formingly knitted polyester fabric has proved to be particularly advantageous in relation to the expectations which the material of the carrier ply 30 is required to meet herein. These woven or loop-formingly knitted fabrics acquire their elasticity through the elasticity of the polyester yarns used. It has to be borne in mind that the slightly elastic fibrous nonwoven polyester webs which are likewise usable here are only sufficiently flexible and elastic in a very thin form which, however, may be inconvenient to die cut and secure to an assembly platform. Woven and loop-formingly knitted polyester fabrics are even in very thick implementations (up to about 150 g/m²) sufficiently stretchable for application as the carrier layer of a plaster while still also being better cuttable or, to be more precise, die cuttable. The unidirectional transverse elasticity of the woven polyester fabric is measured in line with DIN 61632. The elasticity of the material used is advantageously below 150%, preferably in the range from 20 to 80%, more preferably between 40 and 70% and ideally between 44 and 56%. The porosity of the carrier material, i.e., the proportion of a particular reference area which is attributable to pores having an area of less than about 400 µm², is in the range from 10 to 50%. This relative pore area is quantifiable by measuring and counting the pores in some arbitrary unstretched reference area.

In the case of a woven fabric, the backing layer should have from 300 to 350, preferably from 310 to 330, warp threads and/or from 100 to 140, preferably from 120 to 130, weft threads per 10 cm of unstretched fabric.

A further component of the carrier system according to this disclosure is finally formed by the assembly platform 20 which is structurally adhered on the skin remote side of the carrier material and which acts as baseplate to the diagnostic measuring instrument 12. The instrument 12 may for example guide a cannula which has to be positioned as a semi-implant securely in and/or on the body. The combination of carrier ply 30 and assembly platform 20 is exposed to severe mechanical stresses for a prolonged period by the normal movements of the body throughout the period of use, and therefore has to be structurally secured.

Structural adhesives useful for this purpose include epoxy resin adhesives, cyanoacrylates and polyurethane adhesives. Cyanoacrylate adhesives are preferred: they are suitable and approved for use in biomedical engineering, they have very good adherence to different materials, including to surfaces of low surface tension, they are particularly suitable for plastic-plastic bonds and for plastic-metal bonds, they are one pack systems and therefore easily handleable, they are solvent free and they cure very quickly. Factors influencing the curing of cyanoacrylate adhesives include particularly the relative humidity and/or ambient temperatures, the pH of the adherend surfaces, the materials to be bonded together, the width of the glueline, the activator, the viscosity and the cleanliness of the surface. Adhesives of this type are especially used in applications requiring a uniform distribution of stress and high tensile and also shear strength.

UV and moisture curing cyanoacrylates have proved particularly advantageous by virtue of their curing speed and surface drying. A cyanoacrylate based on "ethyl cyanoacrylate" thus was found to be particularly useful for structural type adhesive bonding of plastics, metals and elastomers. The curing process is normally triggered by atmospheric humidity. Full functionality is obtained within a relatively short time, while the cure to the point of full media resistance takes a further 24 h at least. At a temperature of 22° C. and 50% relative humidity the adhesive attains bond strength (shear strength of 0.1 N/mm²) in the course of from 3 to not more than 300 seconds, depending on the material. Rate of cure is dependent on relative humidity. The cure is slowed by a lower and forced by a higher humidity, but the final strength of the adhesive bond is not impaired thereby.

When the rate of cure is relatively slow because of a large joining gap, the cure may be forced by employing an activator. However, this may reduce the final strength of the bond.

The carrier systems which this disclosure provides for adhesive attachment to the skin further comprise a release liner 22 which covers the skin side adhesive layer 34 before use. The tacky area may be completely covered by a one part release liner, but it is also possible for two or more liner strips to each cover the tacky area only partially, although it is in any event preferable for the tacky area to be completely covered. Suitable materials for such release liners are siliconized paper or optionally adhesively coated plastics foils made of for example polyester, polyethylene, polyethylene terephthalate. In the case of a siliconized release liner, the siliconization should also conform to the pertinent foodstuffs and medicolegal regulations.

The carrier system is produced in the following steps:

First the carrier plaster 18 is produced as a cut or, to be more precise, die cut component. To this end, the open width product form of the foundation material, which is in the form of a skin plaster, is cut lengthwise into narrow rolls. These rolls are continuously processed in a rotary die cutting machine featuring two rotating tools. A 50 µm thick polyester liner is laminated together with a weakly adherent processing tape and slit in the first tool, so that a grip tab 24 is obtained. The plaster is then laminated in line onto the polyester liner by removing the original covering. In the second tool, the outer contour of the plaster is incipiently cut and dematrixed, in addition positioning holes 28 are through cut. The process is synchronized using a register control system. The product is then present with the covering with a defined register on the processing tape and can be further processed.

In a further step of the process, the die cut component is connected to the assembly platform 20. For this the assembly platform is first given a pretreatment by application of a primer or of a hydrophilicizing agent before an adhesive bead of the moisture setting cyanoacrylate adhesive with medical approval is applied. Cyanoacrylates with additional UV crosslinking within the reaction time are advantageous here. Subsequently, the VOC emissions of the adhesive are extracted by an air extractor.

In a further step, the plaster is dispensed by a dispenser off the liner and into an interim store and positioned therein. A turning type repositioner then takes the plaster and turns it about 180 degrees. A further repositioner takes the turned plaster and sets it down onto the assembly platform wetted with the adhesive bead and presses the plaster onto the component part. Optionally, the cure which then ensues is hastened from the back with a UV LED areal radiator system.

The carrier system thus obtained is finally placed in a component part carrier and then cured for up to 24 h, depending on the type of adhesive, in a storage unit under constant conditions (temperature, humidity).

Systems according to this disclosure are for example useful for monitoring all possible kinds of bodily functions such as blood sugar, GFR, blood pressure, EEG, heart rate and generally all kinds of clinical parameters, as body entry port systems for administering medicaments or feeding via infusions or pumped systems, as body exit port systems for urine bag or stoma attachments or else as carrier system for body jewelry.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A carrier system for a medical instrument worn on the body, comprising:
    a flexible carrier ply comprising a microperforated thermoplastic foil, the microperforations being formed on the lower side of the carrier ply which faces the skin and at least some of the microperforations being conically shaped and arranged with the wider end of the perforations facing the skin;

the carrier ply having on a lower side thereof an adhesive layer comprising a pressure sensitive adhesive that adheres to the skin of a body part by contact pressure, the adhesive layer having a pressure sensitive adhesive application of 80 to 120 g/m², wherein the microperforations are located on an adhesive covered area of the lower side of the carrier ply; and an assembly platform arranged on an upper side of the carrier ply, wherein the upper side of the carrier ply faces and is attached flatly to a lower joining surface of the assembly platform in a joining region, wherein the joining region is firmly connected to the upper side of the carrier ply via a structural adhesive.

2. The carrier system as claimed in claim 1, wherein the assembly platform has at least one aperture configured for access to the skin.

3. The carrier system of claim 2, wherein the at least one aperture extends through the flexible carrier ply.

4. The carrier system as claimed in claim 1, wherein the carrier ply further comprises a removable release liner.

5. The carrier system as claimed in claim 4, wherein the release liner comprises a projecting tab.

6. The carrier system as claimed in claim 1, wherein the carrier ply has a maximum elastic modulus of less than 10 N/mm².

7. The carrier system as claimed in claim 6, wherein the carrier ply has a maximum elastic modulus of less than 5 N/mm².

8. The carrier system as claimed in claim 1, wherein the adhesive layer has a pressure sensitive adhesive application of 100 to 110 g/m².

9. The carrier system as claimed in claim 1, wherein the adhesive layer is formed by a pressure sensitive adhesive based on acrylate, silicone, rubber, thermoplastic elastomer, hydrogel, polyurethane, polysiloxane, vinyl acetate or mixtures thereof.

10. The carrier system as claimed in claim 1, wherein the carrier ply and/or the adhesive layer has an MVTR value of more than 400 g/m² of water vapor permeability in 24 h.

11. The carrier system as claimed in claim 1, wherein the structural adhesive includes cyanoacrylate, epoxy or polyurethane.

12. The carrier system as claimed in claim 1, wherein the pressure sensitive adhesive and the structural adhesive have a biocompatible composition.

13. The carrier system as claimed in claim 1, wherein the assembly platform is formed by a plastic molding.

14. The carrier system as claimed in claim 13, wherein the assembly platform is formed of polycarbonate.

15. The carrier system of claim 1, wherein the microperforations are wider on the lower side of the carrier ply.

16. The carrier system of claim 1, wherein the microperforations have selectively different perforation geometries.

17. The carrier system as claimed in claim 1, wherein the adhesive covered area of the lower side of the carrier ply is flat.

18. The carrier system of claim 1, wherein the assembly platform is rigid.

19. The carrier system of claim 1, wherein the assembly platform comprises a plate-type plastic molding.

* * * * *